United States Patent [19]

Audibert et al.

[11] 4,153,684

[45] May 8, 1979

[54] IMMUNIZING AND ANTI-INFECTIOUS ADJUVANT AGENTS CONSTITUTED BY N-ACETYL-MURAMYL-L-ALANYL-D-GLUTAMIC ACID DERIVATIVES

[75] Inventors: Françoise Audibert, Neuilly-sur-Seine; Louis Chedid, Paris; Pierre Lefrancier, Bures-sur-Yvette; Jean Choay, Paris; Edgar Lederer, Sceaux, all of France

[73] Assignee: Agence Nationale de Valorisation de la Recherche (ANVAR), Neuilly-sur-Seine, France

[21] Appl. No.: 775,215

[22] Filed: Mar. 7, 1977

Related U.S. Application Data

[63] Continuation-in-part of Ser. No. 516,991, Oct. 22, 1976.

[30] Foreign Application Priority Data

| | | |
|---|---|---|
| Mar. 10, 1976 [FR] | France | 76 06819 |
| Mar. 10, 1976 [FR] | France | 76 06820 |
| Mar. 10, 1976 [FR] | France | 76 06821 |
| Nov. 2, 1976 [GB] | United Kingdom | 45597/76 |
| Jan. 31, 1977 [FR] | France | 77 02646 |

[51] Int. Cl.² ............... A61K 37/02; C07C 103/52
[52] U.S. Cl. ............... 424/88; 260/112.5 R; 424/177; 424/92
[58] Field of Search ............... 260/112.5 R; 424/177, 424/88, 92

[56] References Cited

FOREIGN PATENT DOCUMENTS

2160326  6/1977  France ............... 260/112.5 R

OTHER PUBLICATIONS

Kotani, et al., Biken Journal 18, 105–111 (1975).

*Primary Examiner*—Delbert R. Phillips
*Attorney, Agent, or Firm*—Weiser, Stapler & Spivak

[57] ABSTRACT

The invention relates to new water-soluble agents which are effective as immunizing adjuvants. These adjuvant agents are the methyl, ethyl or propyl esters of 2-(2-acetamido-2-deoxy-3-O-D-glucopyranosyl)-D-propionyl-L-alanyl-D-isoglutamine and of 2-(2-acetamido-2-deoxy-3-O-D-glucopyranosyl)-D-propionyl-L-alanyl-D-glutamic acid, the 2-(2-acetamido-2-deoxy-3-O-D-glucopyranosyl)-D-propionyl-L-alanyl-D-(α-methylamide)-glutamic and 2-(2-acetamido-2-deoxy-3-O-D-glucopyranosyl)-D-propionyl-L-seryl-D-isoglutamine, the 2-(2-acetamido-2-deoxy-3-O-D-glucopyranosyl)-D-propionyl-L-seryl-D-glutamic acid and their derivatives. They are particularly useful to prepare adjuvant medicinal compositions, used for increasing the efficiency of vaccines.

41 Claims, No Drawings

IMMUNIZING AND ANTI-INFECTIOUS ADJUVANT AGENTS CONSTITUTED BY N-ACETYL-MURAMYL-L-ALANYL-D-GLUTAMIC ACID DERIVATIVES

This patent application is a continuation-in-part of pending patent application Ser. No. 516,991, "Compositions of Water Soluble Muropeptides and Methods of Administration," filed Oct. 22, 1976.

The invention relates to water-soluble agents which are effective as immunological adjuvants for promoting immunising responses, or also as anti-infectious agents.

The invention also relates to the medicinal compositions which contain these agents, as well as to the processes for their preparation.

The agents according to the invention are the methyl, ethyl and propyl mono-esters in the α-position, or the methyl, ethyl and propyl diesters of 2-(2-acetamido-2-deoxy-3-O-D-glucopyranosyl)-D-propionyl-L-alanyl-D-glutamic acid, or also the methyl, ethyl and propyl esters of 2-(2-acetamido-2-deoxy-3-O-D-glucopyranosyl)-D-propionyl-L-alanyl-D-isoglutamine.

The compounds correspond to the general formula developed below:

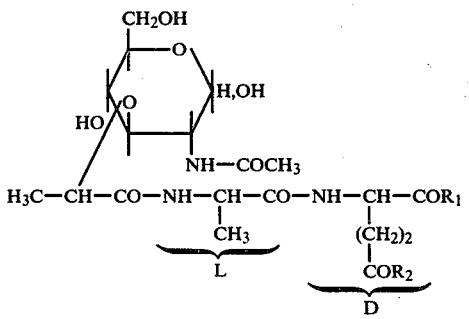

in which $R_1$ is $-OC_nH_{2n+1}$ or $-NH_2$, with $n=1$, 2 or 3, $R_2$ is $-OC_pH_{2p+1}$, with $p=0$, 1, 2 or 3, $p$ not being equal to 0 when $R_1$ is $-NH_2$.

A preferred group of compounds according to the invention is constituted by the mono- (in the α-position) or dimethyl ester of the 2-(2-acetamido-2-deoxy-3-O-D-glucopyranosyl)-D-propionyl-L-alanyl-D-glutamic acid and the methyl ester of the 2-(2-acetamido-2-deoxy-3-O-D-glucopyranosyl)-D-propionyl-L-alanyl-D-isoglutamine, i.e. the compounds for which, in the general formula indicated above, $R_1$ is $-OC_nH_{2n+1}$ with $n=1$, 2 or 3 and $p=0$ or 1, or $R_1$ is $-NH_2$ and $p=1$.

These compounds will subsequently be denoted by the abbreviations
Mur-NAc-L-Ala-D-Glu-α-OCH$_3$
Mur-NAc-L-Ala-D-Glu(OCH$_3$)$_2$
and Mur-NAc-L-Ala-D-iso-Gln(OCH$_3$).

Another adjuvant agent according to the invention is 2-(2-acetamido-2-deoxy-3-O-D-glucopyranosyl)-D-propionyl-L-alanyl-D-(α-methylamide)-glutamic acid, corresponding to the formula

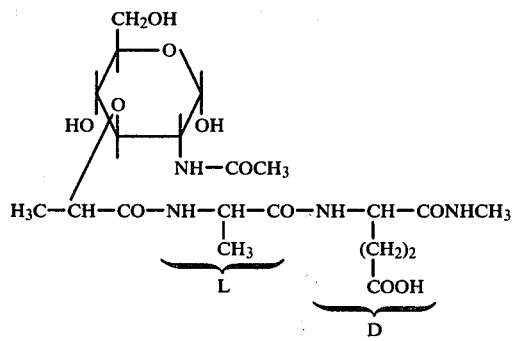

It will be subsequently denoted by the abbreviation Mur-NAc-L-Ala-D-Glu(NHCH$_3$).

Other adjuvant agents according to the invention are 2-(2-acetamido-2-deoxy-3-O-D-glucopyranosyl)-D-propionyl-L-seryl-D-isoglutamine corresponding to the formula

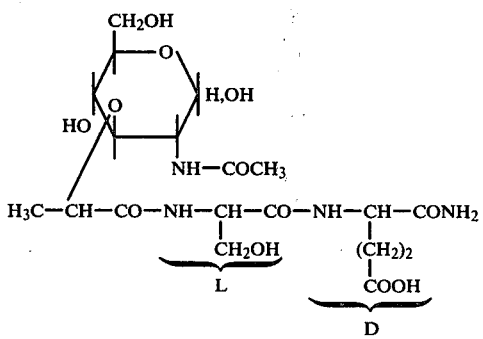

(this will be subsequently denoted by the abbreviation Mur-NAc-L-Ser-D-iso-Gln), and 2-(2-acetamido-2-deoxy-3-O-D-glucopyranosyl)-D-propionyl-L-seryl-D-glutamic acid corresponding to the formula

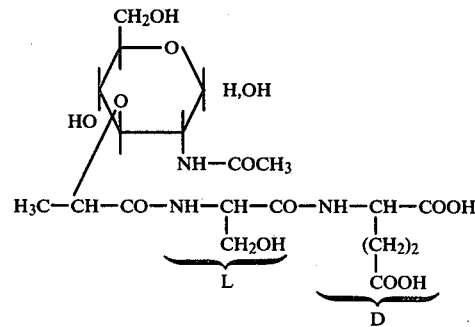

(this will be subsequently denoted by the abbreviation Mur-NAc-L-Ser-D-Glu), their mono and di methyl, ethyl, propyl ester derivatives and their amide derivatives possibly N substituted by methyl rests.

In order to prepare the compounds according to the invention, in a first stage, an equivalent derivative of the fragment corresponding to the peptide chain and to that of the fragment denoted by the abbreviation Mur-NAc is synthesised the functional groups which must not react being first protected, then in a second stage, the coupling of these two derivatives of these fragments is effected. The protecting groups are finally removed, liberating the functions which were previously blocked.

It is also possible to effect the synthesis of these compounds by effecting the separate coupling of a derivative of the Mur-NAc with a derivative of the L-alanine or L-serine, then coupling the resulting product with the equivalent derivative of the glutamic acid or the isoglutamine, according to the processes generally used in peptide synthesis.

The invention also relates to the medicinal compositions containing the said agents and serving especially to increase the action of the weak immunising substances or also to the treatment of infectious diseases. More particularly, the invention concerns compositions containing the said agent which can be used for the immunisation or for the treatment of men and warm-blooded animals so as to prevent or cure bacterial, viral and parasitic infections, or to fight against various organic tissue antigens of normal or pathological origin.

One of the interests of the new products according to the invention is in the fact that it is not necessary to use particular media for their administration on which the manifestation of their pharmacological activity would depend, especially the adjuvant action, and the vehicles with which one is led to associate them have only the object of facilitating the use of these products. In particular, it is not necessary, when these products are injected, to use for this purpose a composition containing an oily phase.

Further, these compounds, which may be used for their adjuvant or anti-infectious action, may be administered orally or parenterally, and especially by injection.

The invention relates in particular to medicinal adjuvant compositions of immunity containing a product of the invention, especially Mur-NAc-L-Ala-D-Glu-α-OCH$_3$, Mur-NAc-L-Ala-D-Glu(OCH$_3$)$_2$ or Mur-NAc-L-Ala-D-iso-Gln(OCH$_3$), Mur-NAc-L-Ala-D-Glu-(NHCH$_3$), Mur-NAc-L-Ser-D-iso-Gln, in association with a pharmaceutically acceptable vehicle. Compositions of this type which are particularly preferred are constituted by injectable solutions containing an effective dose of the product of the invention. Sterile solutions in an aqueous, preferably isotonic, phase, such as saline isotonic solutions or isotonic solutions of glucose, are advantageously used for this purpose. This is of course not restrictive; a simple solution in distilled water can also be used. It is also possible to use injection media containing an oily phase, especially water-in-oil emulsions. Such emulsions are obtained in particular with metabolisable vegetable oils, such as are described in the French Patent Application No. 75 04003. That French patent application corresponds to U.S. co-pending patent application Ser. No. 656,738 of Audibert et al., filed on Feb. 9, 1976, based on said French priority patent application Ser. No. 75-04003.

The adjuvant medicinal compositions of the invention may also be presented in various forms, by using for this purpose vehicles suitable for the selected method of administration. For example, compositions will be used in the form of cachets, compressed tablets or gelatine-coated pills, for oral administration, and aerosols or gels for the application to mucous membranes.

The adjuvant agent may also be in lyophilised form so as to permit the extemporaneous preparation of the adjuvant medicinal compositions.

A pharmaceutically advantageous form comprises unit doses 50 to about 2000 μg, preferably 100 to 800 μg of the adjuvant product according to the invention, and most preferably of about 400 μg.

The invention also includes medicinal compositions in which the products of the invention are associated with an immunising agent, especially a weak vaccinating antigen.

According to another aspect, the invention also concerns medicinal compositions containing the esters of the Mur-NAc-L-Ala-D-Glu and Mur-NAc-L-Ala-D-iso-Gln according to the invention, and especially the Mur-NAc-L-Ala-D-Glu-α-OCH$_3$, the Mur-NAc-L-Ala-D-Glu(OCH$_3$)$_2$ or the Mur-NAc-L-Ala-D-iso-Gln(OCH$_3$), and useful as anti-infectious agents. These products in fact, when they are administered alone, i.e. without vaccinating composition, especially without a weak immunising agent, have shown that they manifest anti-infectious properties of the preventive or even curative type. In other words, the anti-infectious properties are found when these products are administered at the same time that the contamination is accomplished, or even subsequently to this.

These anti-infectious properties are quite unexpected taking into account that one knew beforehand of the activity of the compounds capable of increasing the resistance of the host.

Thus, it is known that one can increase the non-specific resistance to an infection by previously injecting different immunostimulants of bacterial origin, such as certain strains of Corynebacterium, Mycobacteria and their "cord factor", or lipopolyosides (LPS) extracts of gram-negative bacteria. This protection is only manifested, however, on condition of respecting certain intervals of time between the administration of these immunostimulant agents and the moment of the contamination. Thus one has been able to show experimentally that the better percentages of survival in the case of mice infected with Klebsiella are observed when the administration of the immunostimulant is effected about 14 days beforehand for the BCG, about 7 days before for the Corynebacteria, 6 to 48 hours before for the LPS. In all these cases, the immunostimulation by means of these agents must precede the infection. For example, it is well known that, if the LPS is injected at the same time as the inoculum bacteria or after, it produces a "negative reaction" which has a tendency to diminish the resistance of the host who can succumb after the administration of a bacterial strain of even little virulence. On the other hand, when administered under good conditions, these treatments stimulate considerably the non-specific immunity even with regard to strains rendered resistant to antibiotics by mutation or by transfer of plasmides. However, it is difficult or even impossible to use these treatments on account of secondary effects observed after the administration of strong doses of Corynebacteria or of BCG, and above all on account of the toxic effect to man, of the LPS which represents the toxic antigen of the gram-negative bacteria.

On the basis of the results obtained by means of the adjuvant agents of bacterial origin, and especially the tests made with the LPS, it was therefore quite surprising to find that the above-mentioned synthetic adjuvants, according to the invention, show in addition to their adjuvant properties used within the compass of preventive immunising treatments, an anti-infectious activity which is manifested in a preventive, or even curative way, without them being associated with vaccine antigens. These products also have no mitogen activity (absence of blastic transformation of the lymphocytes). They are not antigenic; in fact, they do not release any retarded sensibility reaction in the case of the guinea-pig previously sensitised by means of the Freund complete adjuvant. They have no hyperthermising action with the rabbit for doses much greater than those for which their anti-infectious action is shown. They are negative to the Limulus test and their injection does not cause the death of suprarenalectomised mice although these are rendered extremely sensitive to the lethal effect of the endotoxins by this operation. These results show that these compounds are completely deprived of endotoxic character. They have the advantage of being active considered as anti-infectious agent in the absence of an oily phase, whether the administration is made parenterally or orally, although the adjuvants such as the LPS are only active administered parenterally.

An important advantage of the anti-infectious use according to the invention of the compounds denoted above is the possibility of action against the pathogenic germs which have become resistant to antibiotics following treatments by the traditional antibiotic methods.

It must also be indicated that the anti-infectious curative activity of these compounds is all the more remarkable and unexpected since the tests show that they have no bactericidal or bacteriostatic activity in vitro.

As for the compositions intended to promote the immunising responses, the medicinal compositions containing the above-mentioned methyl esters, and used in anti-infectious therapeutics, can take very varied forms since the properties of the products are shown when the administration is oral or parenteral. The medicinal compositions in particular could be in the form of injectable solutions (especially in the form of isotonic aqueous solutions), drinkable solutions, cachets, gelatine-coated pills, aerosols, gels, etc.

Other characteristics of the invention will appear during the description of examples of preparation of products according to the invention, as well as tests which reveal the pharmacological properties of these products.

In the course of this account, the abbreviations used have the following meanings:
Mur-NAc: 2-acetamido-2-deoxy-3-O-(D-2-propionyl)-D-glucopyranose
Ala: alanine
Glu: glutamic acid
iso-Gln: isoglutamine
4,6-O-bzi: 4,6-O-benzylidene
β-bzl: β-benzyl
BOC: t-butyloxycarbonyl
OBzl: benzyl ester
OSu: succinimide ester
Bzl: benzyl ether Example of synthesis of the 2-(2-acetamido-2-deoxy-3-O-D-glucopyranose)-D-propionyl-L-alanyl-D-glutamic α-methyl ester (a) t-butyloxycarbonyl-L-alanyl-D-glutamic α-benzyl ester (I)

4 g (14 mmoles) of the succinimide ester of BOC-L-alanine, prepared in the manner described by E. Schnabel (Justus Liebig's Ann. Chem. 702, 188 (1967), are dissolved in 15 ml of tetrahydrofuran. This solution is added to an aqueous solution (25 ml) of 3.3 g (14 mmoles) of the γ-benzyl ester of D-glutamic acid, obtained by following the method of S. Guttmann and R. A. Boissenas (Helv. Chim. Acta, 41, 1864 (1958)), and 1.4 g (14 mmoles) of potassium bicarbonate. After one night, the pH is adjusted to 8.5 and the reaction mixture is extracted with ethyl acetate. The aqueous phase is acidified in the cold, to pH 3.5 with a 4 N solution of hydrochloric acid, then it is extracted with ethyl acetate. The organic phase is then washed with water, dried and concentrated. The product is crystallised from an ethyl-acetate-petrol ether mixture. 4.77 g of product are obtained, i.e. a yield of 87.8%. Its physical constants are: M.p. 68°–70° C. $[\alpha]_D^{25} = -12°$ (methanol)

The elementary analysis gives:

| $C_{20}H_{28}O_7N_2$ (408.45) | C % | H % | N % |
|---|---|---|---|
| calculated : | 58.81 | 6.9 | 6.85 |
| found : | 58.7 | 6.4 | 6.8 |

(b) t-butyloxycarbonyl-L-alanyl-D-glutamic α-methyl ester, γ-benzyl ester (II)

408 mg of (I) (1 mmole) are solubilised in 100 ml of anhydrous methanol. An ethereal solution of diazomethane (about 10 mmoles) is added in 15 minutes at 0° C. After 2 hours at ordinary temperature, the reaction mixture is concentrated to dryness and taken up in 25 ml of ethyl acetate. The organic phase is washed successively with a 10% solution of citric acid, water, a 1 M solution of sodium bicarbonate, and water until a neutral pH is obtained. The ethyl acetate phase is dried over $MgSO_4$, filtered and concentrated. An uncrystallisable oil is obtained (385 mg, i.e. a yield of 91%).

(c) The hydrochloride of L-alanyl-D-glutamic α-methyl ester, γ-benzyl ester (III)

385 mg of (II) (0.91 mmole) are treated with 3 ml of an N solution of hydrochloric acid in glacial acetic acid for 30 minutes. The reaction mixture is concentrated to dryness and the oil obtained is dried (330 mg, i.e. a yield of 100%).

(d) 2-(benzyl-2-acetamido-4,6-O-benzylidene-2-deoxy-3-O-α-D-glucopyranosyl)-D-propionyl-L-alanyl-D-glutamic α-methyl ester, γ-benzyl ester (IV)

473 mg (1 mmole) of benzyl-2-acetamido-4,6-benzylidene-3-O-(D-carboxyethyl)-2-deoxy-α-D-glucopyranoside, prepared in the way described by Flowers and R. W. Jeanloz (J. Org. Chem. 28, 2983 (1963)), are dissolved in 5 ml of dimethylformamide cooled to −15° C. 0.11 ml (1 mmole) of N-methylmorpholine and 0.13 ml (1 mmole) of isobutyl chlorocarbonate are successively added.

To this reaction mixture is added a solution of 330 mg (0.9 mmole) of (III) and 0.1 ml (0.9 mmole) of N-methyl-morpholine in 5 ml of dimethylformamide, previously cooled to −15° C.

After one night at −15° C., 1 ml of a 2.5 N solution of potassium bicarbonate is added. After 30 minutes, the product is precipitated by addition of 40 ml of distilled water, filtered off and dried. 667 mg of product are obtained, i.e. a yield of 95.5%.

(e) 2-(2-acetamido-2-deoxy-3-O-D-glucopyranose)-D-propionyl-L-alanyl-D-glutamic α-methyl ester (V)

305 mg of (IV) (0.39 mmole) are hydrogenated for 15 hours in solution in 50 ml of glacial acetic acid, in the presence of 300 mg of 5% palladium on charcoal. After filtration of the catalyst, then concentration to dryness of the acetic acid, the product is precipitated from methanol-acetone-ether, then centrifuged. 140 mg are obtained, i.e. a yield of 70%. The product is purified by chromatography on a column (2×10 cm) filled with an ion-exchanger resin, commercialised under the name AG1X-2 by the BIORAD Company (acetate form). It is eluted with a 0.2 M solution of acetic acid, the interesting fractions are united and lyophilised. 117 mg are recovered, i.e. a yield of 83.5%, of a product of which the rotatory power is $[\alpha]_D^{25} = +39°$ (methanol). The product is finally obtained after passage over a column (2×80 cm), filled with ion-exchanger commercialised under the name of SEPHADEX G.15 by PHARMACIA UPSALA (elution with acetic acid 0.2 M) and lyophilisation of the fractions of interest. At the end 94 mg of product (V) are obtained, i.e. a yield of 80%. The rotatory power remains at $[\alpha]_D^{25} = +39°$ (methanol), and the elementary analysis thereof is:

| $C_{20}H_{33}O_{12}N_3$, $1H_2O$ (525.50) | C % | H % | N % |
| --- | --- | --- | --- |
| calculated : | 45.7 | 6.7 | 7.99 |
| found : | 44.93 | 6.32 | 7.91 |

Example of synthesis of the 2-(2-acetamido-2-deoxy-3-O-D-glucopyranose)-D-propionyl-L-alanyl-D-glutamic dimethyl ester In a first stage, the Mur-NAc-L-Ala-D-Glu is prepared in the following way:

(a) Preparation of the benzyl diester of the BOC-L-alanyl-D-glutamic acid (A)

2.3 g (8 mmoles) of succinimide ester of t-butyloxycarbonyl-L-alanine, the amine function of which is protected by the t-butyloxycarbonyl group (BOC-L-Ala-OSu), are added with stirring to a solution in dimethylformamide of 4.5 g (9 mmoles) of the p-toluene-sulphonate of the benzyl diester of D-glutamic acid and 1 ml (9 mmoles) of N-methylmorpholine. The reaction mixture is left for 12 hours at the ambient temperature. It is then concentrated to dryness. The dry compound is taken up in 50 ml of ethyl acetate and washed successively with a 10% solution of citric acid, water, with a solution of 1 N sodium bicarbonate, and finally with water. The ethyl acetate phase is dried over MgSO$_4$, filtered and concentrated. On crystallising from a mixture of ethyl acetate and hexane, 2.50 g (67.5%) are obtained of the desired product of which the physical constants are:
M.p. 105°–106° C.
$\alpha_D^{25} = +7.3°$
The elementary analysis of this product is:

| $C_{27}H_{34}O_7N_2$ (498.5) | C % | H % | N % |
| --- | --- | --- | --- |
| calculated : | 65 | 6.9 | 5.6 |
| found : | 64.85 | 7.0 | 5.5 |

(b) Preparation of the benzyl diester of the 2-(2-benzyl-2-acetamido-4,6-benzylidene-2-deoxy-3-O-D-glucopyranosyl)-D-propionyl-(O-benzyl)-L-alanyl-D-glutamic acid (B)

500 mg (1 mmole) of compound (A) are treated with 5 ml of a 1 N solution of hydrochloric acid in glacial acetic acid. After 30 minutes, the reaction mixture is concentrated to dryness. The oil obtained is taken up in 25 ml of an acetonitriledimethylformamide mixture (2/1, v/v). The mixture is cooled to 0° C. and 0.141 ml (1 mmole) of triethylamine is added. The solution prepared is poured with stirring at 0° C. into a suspension prepared 1.5 hours before and formed from 472 mg (1 mmole) of benzyl-2-acetamido-4,6-O-benzylidene-3-O-(D-1 carboxyethyl)-2-deoxy-β-D-glucopyranoside and 0.141 ml (1 mmole) of triethylamine in 25 ml of the acetonitrile-dimethylformamide mixture (2/1, v/v).

The mixture is left for 12 hours at the ambient temperature; it is then concentrated and the residue is precipitated in a 10% solution of citric acid. The precipitate is filtered off, washed copiously with water and dried. 800 mg (94%) are obtained of the desired product the constants of which are:
M.p. 198°–199° C.
$\alpha_D^{25} = 4.92°$ (dimethylformamide)
After recrystallisation from ethanol, the melting point is established at 220° C.
The elementary analysis of this product is:

| $C_{47}H_{53}O_{12}N_3$ (851.96) | C % | H % | N % |
| --- | --- | --- | --- |
| calculated : | 66.26 | 6.27 | 4.93 |
| found : | 66.34 | 6.45 | 4.92 |

(c) Preparation of the 2-(2-acetamido-2-deoxy-3-O-D-glucopyranosyl)-D-propionyl-L-alanyl-D-glutamic acid (C) or Mur-NAc-L-Ala-D-Glu 700 mg (0.8 mmole) of the compound (B) are treated with 40 ml of a 60% solution of acetic acid on a boiling water-bath for 1 hour. The reaction mixture is then concentrated to dryness (then dried over MgSO$_4$). The residue is taken up in 1 ml of a chloroform-methanol mixture (3/3, v/v) and placed on a silica column (35 g) previously equilibrated with the same solvent mixture. The fractions containing the product are collected and concentrated to dryness (their homogeneity is tested by chromatography on a thin layer of silica gel in the same mixture of solvents). 185 mg (30%) of derivative are obtained.

76 mg of this derivative are dissolved in 15 ml of glacial acetic acid, then subjected to a hydrogenation in the presence of 5% palladium on charcoal. After filtration, the mixture is concentrated to dryness and precipitated in a methanol-acetone-ether mixture. 45 mg (92%) of the desired product are thus obtained, of which the constants are:
M.p. 150°–155° C.
$\alpha_D^{25} = +33°$ (glacial acetic acid)
The elementary analysis of this product is:

| $C_{19}H_{31}O_{12}N_3 1H_2O$ (511.48) | C % | H % | N % |
| --- | --- | --- | --- |
| calculated : | 44.6 | 8.2 | 6.5 |
| found : | 44.7 | 8.1 | 6.4 |

In a second stage, the previously prepared Mur-NAc-L-Ala-D-Glu is esterified.

100 mg (0.2 mmole) of Mur-NAc-L-Ala-D-Glu are dissolved in 10 ml of absolute methanol. In 15 minutes, 10 ml of an ethereal solution of diazomethane (about 0.7 mmole per ml) are added. After 90 minutes, a drop of acetic acid is added and the reaction mixture is concentrated to dryness. The residue obtained is purified on a column of silica gel (1×16 cm), with for solvent the mixture chloroform-methanol (6/2, v/v). The pure fractions are united and concentrated. The product is precipitated from a methanol-acetone-ether mixture. 83 mg of product (yield 80%) are obtained, of which the constants are:

M.p. 137°–142° C.

$a_D{}^{25} = +31.6°$ (glacial acetic acid)

The elementary analysis is as follows:

| $C_{21}H_{35}O_{12}N_3$ (521.53) | C % | H % | N % |
|---|---|---|---|
| Calculated : | 48.36 | 6.76 | 8.57 |
| found : | 48.0 | 7.0 | 8.2 |

Example of synthesis of the 2-(2-acetamido-2-deoxy-3-O-D-glucopyranose)-D-propionyl-L-alanyl-D-isoglutamine methyl ester For the preparation of this product, the Mur-NAc-L-Ala-D-iso-Gln obtained in the way described in the French Patent Application No. 74 22909 is used.

100 mg (0.2 mmole) of Mur-NAc-L-Ala-D-iso-Gln are treated in the way previously described for the esterification of the Mur-NAc-L-Ala-D-Glu. The purification is effected by means of the chloroform-methanol mixture (5/5, v/v). 80 mg of product are obtained (80% of yield) of which the constants are:

M.p. 201° C.

$a_D{}^{25} = +44.2°$ (glacial acetic acid)

The elementary analysis of this product is:

| $C_{20}H_{34}O_{11}N_4$ (506.52) | C % | H % | N % |
|---|---|---|---|
| calculated: | 47.52 | 6.76 | 11.06 |
| found : | 47 | 6.5 | 10.3 |

Pharmacological properties of the esters of Mur-NAc-L-Ala-D-Glu and Mur-NAc-L-Ala-D-iso-Gln (1) Toxicity The toxicity of the products according to the invention has been studied by parenteral administration to mice and rabbits. It was found that the toxic doses are of an order of magnitude much greater than that of the doses at which these products show their activity. Thus, these products are well tolerated by mice at doses equal to or greater than 100 mg/kg of animal, and by rabbits at doses equal to or greater than 5 mg/kg of animal.

(2) Adjuvant character of the Mur-NAc-L-Ala-D-Glu-α-OCH₃, of the Mur-NAc-L-Ala-D-Glu(OCH₃)₂ and of the Mur-NAc-L-Ala-D-iso-Gln(OCH₃) in aqueous phase In the series of tests of which the results are indicated hereafter, the influence of the active principle according to the invention on the proportion of the anti-albumin antibody has been studied under the following conditions.

Groups of 8 Swiss mice aged two months receive by subcutaneous injection (SC) or orally (PO) 0.5 mg of antigen constituted by the albumin of bovine serum (BSA) with or without the substance tested in an isotonic saline solution. This large dose of antigen, since it is situated at the limit of the paralysing dose with respect to the immunising response, on account of this fact has a weak response or no response to the antigen alone in the case of the controls; it therefore constitutes a severe criterion for showing the activity of an adjuvant substance. Thirty days later, the mice receive, by the same method of administration, a further dose containing 0.1 mg of the same antigen.

The proportion of antibody is determined by passive hemagglutination by using the red blood corpuscles of sheep treated with formalin and recovered from the antigen studied according to the method described by A. A. Hirata and M. W. Brandiss (J. Immunol., 100, 641–648, 1968). The taking of the blood occurred 14, 28, 34 and 36 days after the first injection.

By way of comparison, mice receive, instead of the product according to the invention, either lipopolysaccharides (LPS) (extract of S.Enteritidis by the water-phenol method), or the adjuvant denoted by the name "WSA" and described by Adam et al. [Infect. Immun. (1973) 7, 855–861]. The control mice only receive the antigen.

The results of these tests are given in the following Table. The proportions of antibody express the maximum serum dilution which agglutinates a given quantity of red blood corpuscles of sheep.

Table 1

|  |  | Administration | Proportion of antibody | | | |
|---|---|---|---|---|---|---|
|  |  |  | 14th day | 28th day | 34th day | 36th day |
| BSA controls |  | S.C. | <3 | 3 | 3 | 20 |
| BSA + LPS | (100µg) | S.C. | <3 | 6 | 50 | 1310 |
| BSA + WSA | (300µg) | S.C. | <3 | <3 | <3 | 6 |
| BSA + Mur-NAc-L-Ala-D-Glu-α-OCH₃ | (100µg) | S.C. | 12 | 12 | 200 | 400 |
| BSA + Mur-NAc-L-Ala-D-Glu-α-OCH₃ | (10µg) | S.C. | 6 | 6 | 200 | 400 |
| BSA + Mur-NAc-L-Ala-D-Glu-α-OCH₃ | (2000µg) | P.O. | 6 | 6 | 50 | 200 |
| BSA + Mur-NAc-L-Ala-D-iso-Gln(OCH₃) | (100µg) | S.C. | 12 | 12 | 100 | 800 |
| BSA + Mur-Nac-L-Ala-D-Glu-(OCH₃)₂ | (100µg) | S.C. | 50 | 50 | 400 | 800 |

These results show that the products of the invention, administered in isotonic saline solution, cause a large increase of the proportion of antibody formed, even in the case where the adjuvant is orally administered.

The active principles according to the invention engender responses which may be considered in a general way as comparable to those that are obtained with the "LPS", but it must be remarked that, contrary to the latter, they have no toxicity.

(3) Adjuvant character of the Mur-NAc-L-Ala-D-Glu-α-OCH₃, of the Mur-NAc-L-Ala-D-Glu(OCH₃)₂ and of the Mur-NAc-L-Ala-D-iso-Gln(OCH₃) in the presence of an oily phase In these tests, the increase of the proportion of antibody specific to a given antigen is followed when the latter is injected, with or without the adjuvant compound according to the invention, in a water-in-oil emulsion.

The tests are effected on batches of 6 Hartley guinea-pigs, females, of 350 g. The administration is made by intradermal injection in the planter pad of each of the hind feet. The ovalbumin (constituting the antigen) at the rate of 1 mg or 0.5 mg is prepared in 0.1 ml. of an emulsion of saline isotonic solution, in an oily phase constituted either by the Freund incomplete adjuvant (FIA) or by the complete adjuvant (FCA) formed by the FIA to which is added 0.1 mg of entire cells of Mycobacterium smegmatis. The compound according to the invention is administered at the rate of 0.1 mg contained in the emulsion containing the FIA.

Eighteen days after this immunisation, one looks for possible reactions of retarded hypersensitivity in the antigen on injecting indradermally 0.01 mg or 5 μg of ovalbumin on the side of the animals, and 48 hours after, the reaction at the point of injection is observed. The diameter in mm of the reaction thus caused is measured.

Tweny-one days after the injection, the animals are bled. On the serum collected is measured the content of antibody specific to the ovalbumin by precipitation of the complex antibody-antigen in the zone of equivalence. The quantity of protein nitrogen contained in this precipitate is evaluated according to the method of Folin. The average values of the contents of antibody are indicated in the Table of results.

These values express the quantity, in microgrammes, of nitrogen which can be precipitated by the antigen, per ml of serum. In some cases, the antibody level has been determined too by passive hemagglutination (PHA) as above indicated.

The results of these tests are reported in the following Table 2.

following the inoculation. After eight days, the survival of the animals is finally ascertained.

The survival of groups of mice inoculated under the conditions indicated above and treated by means of the methyl ester considered was followed.

By way of comparison, batches of mice have been treated with BCG and LPS. This latter, as is known, is an extremely active immunostimulant when it is administered 24 hours before the infection.

For these tests, hybrid mice (C57B1/6×AKR)F1, reared at the PASTEUR INSTITUTE, from strains coming from the breeding of the C.N.R.S. at Orleans, were used. The endotoxin or LPS was extracted by the phenol-water method from *Salmonella enteritidis* variety Danysz (No. 5629, PASTEUR INSTITUTE). The BCG comes from the strain *Mycobacterium tuberculosis* var. bovis (No. 1173 $P_2$ of the PASTEUR INSTITUTE), cultivated on Sauton medium and killed by a solution of 2% of phenol.

The infection by *Klebsiella pneumoniae*, strain of capsular type 2, biotype d, is made from a culture of 16 hours in a medium for pneumococcus (No. 53515, PASTEUR INSTITUTE). The preparations injected before or at the moment of the infection are always diluted in apyrogenic physiological solution, at the rate of 0.2 ml for parenteral administration and 0.5 ml for oral admin- Table 2

| Composition of the emulsion containing the antigen | Serum antibody | | |
|---|---|---|---|
| | Precipitation (μg/ml) | Agglutination | Cutaneous test (diameter in mm) |
| ovalbumin (1 mg) + FIA | <500 | — | 0 |
| ovalbumin (1 mg) + FCA (100μg) | 3200 | — | 10 ± 1.5 |
| ovalbumin (1 mg) + FIA + Mur-Nac-L-Ala-D-Glu-α-OCH$_3$ (100μg) | 2600 | — | 6 ± 3 |
| ovalbumin (0.5 mg) + FIA | ≧500 | 900 | 0 |
| ovalbumin (0.5 mg) + FCA (100μg) | 2100 | 3600 | 13.5 |
| ovalbumin (0.5 mg) + FIA + Mur-NAc-L-Ala-D-iso-Gln(OCH$_3$) (100 μg) | 2100 | 3000 | 12 |
| ovalbumin (0.5 mg) + FIA + Mur-Nac-L-Ala-D-Glu(OCH$_3$)$_2$ (100μg) | 950 | 2600 | 6.2 |

These results show that the compounds of the invention, administered in an oily emulsion, have an influence on the proportion of antibody formed in response to the injection of antigen, and that it induces a reaction of retarded hypersensitivity with respect to the same antigen.

(4) Anti-infectious character

The following tests illustrate the anti-infectious properties of the Mur-NAc-L-Ala-D-Glu-α-OCH$_3$, of the Mur-NAc-L-Ala-D-Glu(OCH$_3$)$_2$ and of the Mur-NAc-L-Ala-D-iso-Gln(OCH$_3$).

In the preliminary tests, an experimental method was established permitting the anti-infectious character of the products to be shown. It has thus been shown that a dose of $10^4$ *Klebsiella pneumoniae*, injected intramuscularly in mice, produced the progressive decease of a large part, if not the whole, of the animals in the week istration, the controls receiving the solution alone.

In the tests of which the results are reported in the Tables 3 and 4, the influence of the treatment by varying the methods, the doses and the time of administration of the products studied has been determined. The percentage of protection expresses the difference of the percentages of survivors in the group of treated animals with respect to the corresponding control group.

The results show that the products studied have an anti-infectious activity, whether they are administered parenterally or orally. On the contrary, the LPS is inactive when given orally, even for the very large doses (100 μg of LPS represent 10000 times the anti-infectious dose taken parenterally.

In addition, the results are the same if the products are administered 24 hours or only 1 hour before the infectant injection, administered intramuscularly.

Table 3

| | Anti-infectious protection with respect to an intramuscular inoculation of $10^4$ K.pneumoniae Treatment 24 hours before the infection | | | | |
|---|---|---|---|---|---|
| Method of treatment | Number of animals treated | Number of animals surviving on day | | | % of protection |
| | | 3 | 5 | 8 | |
| Control | 24 | 12 | 8 | 2 | |

Table 3-continued

Anti-infectious protection with respect to an intramuscular inoculation of $10^4$ K.pneumoniae
Treatment 24 hours before the infection

| Method of treatment | | | Number of animals treated | Number of animals surviving on day | | | % of protection |
|---|---|---|---|---|---|---|---|
| | | | | 3 | 5 | 8 | |
| | LPS | 1 μg | 24 | 24 | 22 | 22 | 83 |
| | Control | | 24 | 11 | 9 | 6 | |
| | BCG | 100 μg | 24 | 24 | 24 | 21 | 63 |
| | control | | 24 | 15 | 11 | 7 | |
| | Mur-NAc-L-Ala-D-Glu- | | | | | | |
| I.V. | α-OCH$_3$ | 100 μg | 24 | 24 | 24 | 23 | 67 |
| | Control | | 24 | 13 | 9 | 4 | |
| | Mur-NAc-L-Ala-D-Gln-OCH$_3$ | 100 μg | 24 | 21 | 3 | 11 | 29 |
| | Control | | 24 | 13 | 9 | 4 | |
| | Mur-NAc-L-Ala-D-Glu-(OCH$_3$)$_2$ | 100 μg | 24 | 21 | 19 | 15 | 46 |
| | Control | | 12 | 6 | 4 | 2 | |
| | Mur-NAc-L-Ala-D-Glu-α-OCH$_3$ | 2000 μg | 12 | 11 | 9 | 6 | 40.5 |
| | Control | | 2 | 6 | 5 | 2 | |
| per os | Mur-NAc-L-Ala-D-Glu-(OCH$_3$)$_2$ | 2000 μg | 12 | 10 | 9 | 8 | 50 |
| | Control | | 24 | 14 | 10 | 7 | |
| | LPS | 100 μg | 24 | 13 | 10 | 8 | |

Table 4

Anti-infectious protection with respect to an intramuscular inoculation of $10^4$ K.pneumoniae
Treatment 1 hour after the infection

| Method of treatment | | | Number of animals treated | Number of animals surviving on day | | | % of protection |
|---|---|---|---|---|---|---|---|
| | | | | 3 | 5 | 8 | |
| | Control | | 16 | 6 | 2 | 1 | |
| | Mur-NAc-L-Ala-D-Glu-α-OCH$_3$ | 100 μg | 16 | 16 | 16 | 14 | 88 |
| I.V. | Control | | 8 | 6 | 5 | 1 | |
| | Mur-NAc-L-Ala-D-Glu(OCH$_3$)$_2$ | 100 μg | 8 | 8 | 8 | 8 | 88 |
| | Control | | 16 | 10 | 6 | 1 | |
| | BCG | 100 μg | 16 | 14 | 13 | 10 | 50 |

In another series of tests, the anti-infectious properties of the products were studied with respect to a very violent infection caused by the intravenous injection (and not intramuscular) of $10^3$ K. pneumoniae.

In these tests, also effected on mice, the treatments are effected 24 hours before the inoculation. The methods and the doses are indicated in Table 5 in which the results of these tests are reported.

Table 5 i-infections protection with respect to an intravenous inoculation of $10^3$ K.pneumoniae
Treatment 24 hours before the infection

| Method of treatment | | | Number of animals treated | of animals surviving on day | | | % of protection |
|---|---|---|---|---|---|---|---|
| | | | | 3 | 5 | 8 | |
| I.V. | Mur-NAc-L-Ala-D-Glu-α-OCH$_3$ | 100 μg | 16 | 16 | 16 | 12 | 65 |
| I.V. | Mur-NAc-L-Ala-D-Glu-(OCH$_3$)$_2$ | 100 μg | 16 | 15 | 12 | 10 | 52.5 |
| I.V. | LPS | 1 μg | 16 | 16 | 16 | 16 | 90 |
| I.V. | BCG | 100 μg | 16 | 16 | 16 | 16 | 90 |
| per os | BCG | 2000 μg | 16 | 3 | 0 | | |

The results show a significant protection in the case of mice treated by means of the products according to the invention.

Example of synthesis of the Mur-NAc-L-Ala-D-Glu(NHCH$_3$)

BOC-D-Glu(NHCH$_3$)-OBzl (A)

3.36 g (10 mmole) of the benzyl γ-ester of BOC-D-Glu [E. Schröder, E. Klieger, Justus Liebig's Ann. Chem. 673, 1964)196] are dissolved in 50 ml of tetrahydrofuran. 1.1 ml (10 mmoles) of N-methylmorpholine and 1.3 ml (10 mmoles) of isobutyl chloroformate are added while stirring to the solution cooled to −15° C. After 10 minutes and at 0° C., a stream of dry methylamine is passed into the suspension. After 60 minutes, the reaction mixture is increased to 150 ml with addition of ethyl acetate, and the organic phase is washed with water until the pH is neutral, then dried over MgSO$_4$. After filtration, the ethyl acetate phase is concentrated to dryness and the product is precipitated with ether. 2.8. g of product are obtained, i.e. a yield of 80%. The constants of this product are:

M.p. 124°–126° C.
$\alpha_D^{25} = +1.4°$ (absolute methanol)
The elementary analYsis of the product is:

| $C_{18}H_{26}O_5N_2$ (350.42) | C % | H % | N % |
|---|---|---|---|
| calculated : | 61.69 | 7.48 | 7.99 |
| found : | 62 | 7.6 | 8.2 |

Hydrochloride of D-Glu(NHCH$_3$)-OBzl (B)

1.4 g (4 mmoles) of (A) are treated with 12 ml of an approximately N solution of hydrochloric acid in acetic acid, for 30 minutes. The reaction mixture is concentrated to dryness. The product is obtained in the form of an oil. It is homogeneous on chromatography on a thin layer of silica gel in n-butanol-pyridine-acetic acid-water (30/20/6/24, v/v).

BOC-L-Ala-D-Glu(NHCH$_3$)-OBzl (C)

1 g (3.5 mmoles) of the succinimide ester of BOC-Ala-[G. W. Anderson, J. E. Zimmerman, F. M. Callahan, J. Amer. Chem. Soc. 86 (1964) 1839] is added to a solution in dimethylformamide (10 ml), cooled to 0° C., of 3.7 mmoles of (B) and 0.4 ml (3.7 mmoles) of N-methylmorpholine. After a night at the ambient temperature, the reaction mixture is concentrated to dryness and taken up in 100 ml of ethyl acetate. The organic phase is washed successively with a 10% solution of citric acid, water, a N solution of CO$_3$HNa, then with water to a neutral pH. The ethyl acetate phase is dried for 30 minutes over MgSO$_4$, then filtered and concentrated to dryness. The product is crystallised in a methanol-petrol ether mixture. 1.04 g are obtained, i.e. a yield of 71%. The constants of this product are:
M.p. 145°-147° C.
$\alpha_D{}^{25} = +6.4°$ (glacial acetic acid)
The elementary analysis of the product is:

| $C_{21}H_{31}O_6N_3$ (421.50) | C % | H % | O % | N % |
|---|---|---|---|---|
| calculated : | 59.84 | 7.41 | 22.77 | 9.97 |
| found : | 60.2 | 7.4 | 22.82 | 10.01 |

Hydrochloride of L-Ala-D-Glu(NHCH$_3$-OBzl (D)

842 mg (2 mmoles) of (C) are treated for 30 minutes with 5 ml of an approximately N solution of hydrochloric acid in acetic acid. The reaction mixture is concentrated to dryness and the residue purified by chromatography on a column of silica gel (35 g) (CHCl$_3$-MeOH, 5/5, v/v). The pure fractions obtained are united and concentrated. 614 mg of product in the form of oil are obtained, i.e. a yield of 86%.

Mur-NAc ($\beta$-bzl-4,6-bzi)-L-Ala-D-Glu(NHCH$_3$)OBzl (E)

377 mg (0.8 mmoles) of Mur-Nac ($\beta$-bzl-4,6-bzi) are added to a solution in 10 ml of dimethylformamide of 0.86 mmole of (D) and 0.1 ml (0.86 mmole) of N-methylmorpholine. 108 mg (0.8 mmole) of hydroxybenzotriazole and 165 mg (0.8 mmole) of dicyclohexylcarbodiimide are added. After a night at the ambient temperature, the product and the dicyclohexylurea formed are precipitated in water, filtered and dried. 767 mg of precipitate are thus obtained, i.e. a yield of 96%.

380 mg of the precipitate are purified on a column of silica gel (30 g). The column is eluted first with chloroform, then with a chloroform-methanol mixture (5/5, v/v). The pure fractions are united and concentrated. 250 mg of product are thus obtained (yield 80%) of which the rotatory power is:
$\alpha_D{}^{25} = -17°$ (dimethylformamide)
The elementary analysis of the product is as follows:

| $C_{41}H_{50}O_{11}N_4$—0.75 H$_2$O (792.88) | C% | H% | N% |
|---|---|---|---|
| calculated : | 62.46 | 6.65 | 7.10 |
| found : | 62.7 | 6.69 | 6.92 |

Mur-NAc-L-Ala-D-Glu(NHCH$_3$) (F)

198.22 mg (0.25 mmole) of (E), dissolved in 15 ml of glacial acetic acid, are hydrogenated for 10 hours in the presence of palladium on charcoal. After filtration of the catalyst and concentration to dryness of the reaction mixture, the product is obtained by precipitation from the ethanol-acetone-ether mixture. 108 mg of product (yield 85%) are obtained, of which the constants are:
M.p. 157°-161° C.
$\alpha_D{}^{25} = +49°$ (glacial acetic acid)
The product is chromatographically homogeneous on plates of silica gel in n-butanol-pyridine-acetic acid-water (30/20/6/24, v/v) and n-butanol-acetic acid-water (4/1/5, v/v upper phase) mixtures. The elementary analysis is as follows:

| $C_{20}H_{34}O_{11}N_4$ (506.52) | C% | H% | N% |
|---|---|---|---|
| calculated : | 47.42 | 6.76 | 11.06 |
| found : | 47.5 | 6.8 | 11.0 |

Pharmacological properties of the Mur-NAc-L-Ala-D-Glu(NHCH$_3$)

The harmlessness, or on the contrary the toxicity of the product of the invention, is studied by intravenous injection on mice aged two months. On progressively increasing the doses administered, that is determined for which the mortality of the mice of a single batch is established at 50% (LD$_{50}$).

For the product studied, it was shown that the LD$_{50}$ is greater than 1 g per kg of animal, which is much greater than the doses for which the product shows its adjuvant properties.

Adjuvant character in aqueous solution

In the series of tests of which the results are indicated hereafter, the influence of the active principle according to the invention on the strength of the anti-albumin antibodies under the following conditions was studied.

Groups of 8 Swiss mice aged two months receive, by subcutaneous injection, 0.5 mg of antigen constituted by the albumin of bovine serum (BSA) and 0.1 mg of the substance tested in an isotonic saline solution. This large dose of antigen, since it is situated at the limit of the paralysing dose with respect to the immunising response, on account of this fact, has a weak response or no response to the anitgen alone in the case of the controls; it therefore constitutes a severe criterion for showing the activity of an adjuvant substance. Thirty days later, the mice receive a further dose containing 0.1 mg of the same antigen.

The strength of antibody is determined by passive hemagglutination, by using the red blood corpuscles of sheep treated for formalin and recovered from the antigen studied by the method described by A. A. Hirata and M. W. Brandiss (J. Immunol., 100, 641-648, 1968). The taking of the blood took place 14, 28, 34 and 36 days after the first injection.

By way of comparison, mice receive, instead of Mur-NAc-L-Ala-D-Glu(NHCH$_3$), either lipopolysaccharides (LPS) (extract of *S. Enteritidis* by the water-phenol method), or the adjuvant denoted by the name "WSA" and described by Adam et al. [Infect. Immun. (1973 (7, 885–861]. The control mice only receive the antigen.

The results of these tests are given in the following Table.

Table 1

| strength of anti body | 14th day | 28th day | 34th day | day |
|---|---|---|---|---|
| Control - BSA | <3 | <3 | <3 | <3 |
| BSA + LPS (100 μg) | <3 | 6 | 50 | 1310 |
| BSA + WSA (300 μg) | <3 | <3 | <3 | 6 |
| BSA + Mur-NAc-L-Ala-D-Glu (NHCH$_3$) (100μg) | 6 | 1600 | 1600 | |

These results show that the Mur-NAc-L-Ala-D-Glu(NHCH$_3$), administered in isotonic saline solution, causes a considerable increase of the proportion of antibody formed, although, under the same conditions, the "WSA" is practically inactive. The responses obtained with the Mur-NAc-L-Ala-D-Glu(NHCH$_3$) can be considered in a general way as comparable to those which are found with the "LPS", but it must be remarked that, contrary to the latter, it has no toxicity.

Adjuvant character in the presence of an oily phase

As for the preceding tests, one follows the increase of the proportion of antibody caused by the injection of antigen and of the compound of the invention, but, in the present case, the injection contains an oily phase constituted by Freund's incomplete adjuvant (in water-in-oil emulsion).

For these tests, Hartley guinea-pigs of 350 g were used. The control animals receive, in each of the hind feet 0.1 ml of emulsion, either of FIA, or of FCA (Freund's complete adjuvant) containing 500 μg of ovalbumin (antigen). The test product is administered at the rate of 100 μg, in an emulsion of FIA.

21 days after the injection, the proportion of antibody is determined by passive hemagglutatination (PHA), as previously, and by precipitation by the method of Folin.

The same guinea-pigs undergo 18 days after the injection a test of cutaneous hypersensitivity. For this purpose, they receive by intradermic injection, 5 μg of ovalbumin. 48 hours after this injection, the diameter of the induration at the point of injection is measured.

The results are given in the following Table:

Table 2

| Injection | Proportion of antibody Precipitation | Agglutination | Cutaneous Tests diameter in mm) |
|---|---|---|---|
| ovalbumin + FIA | ≦500 | 900 | 0, 0, 0, 0, 0, 0 |
| ovalbumin + FCA | 2100 | 3 600 | 12,13,12,14,11,19 |
| ovalbumin + FIA + Mur-NAc-L-Ala-D-Glu(NHCH$_3$) | 5500 | 6100 | 8, 9, 14, 15, 15 |

These results show that the Mur-NAc-L-Ala-D-Glu(NHCH$_3$), administered in the presence of an oily phase, promotes to a very large extent the increase of the proportion of antibody, and that it induces a hypersensitivity reaction of the retarded type with respect to the same antigen.

Example of synthesis of the Mur-NAc-L-Ser-D-iso-Gln

BOC-L-Ser (Bzl)-D-iso-Gln-OBzl (I)

1.48 g (5 mmoles) of BOC-L-Ser (Bzl) [E. Wünsch, A. Zwick, Chem. Ber. 97 (1964)2497] are added with stirring to a solution in dimethylformamide of 1.64 g (6 mmoles) of the hydrochloride of the benzyl ester of D-isoglutamine [P. Lefrancier, E. Bricas, Bull. Soc. Chim. France (1969) 3561] and of 0.66 ml (6 mmoles) of N-methylmorpholine. 1.24 g (6 mmoles) of NN'-dicyclohexyl-carbodiimide are added, and the reaction mixture is left at the ambient temperature for 12 hours. It is then concentrated and taken up in 50 ml of ethyl acetate and the organic phase is washed successively with a 10% solution of citric acid in water, an N solution of sodium bicarbonate, then with water until a neutral pH is obtained. The ethyl acetate phase is dried over MgSO$_4$, then concentrated. The product is crystallised from an ether-petrol ether mixture. 1.40 g of product are obtained, i.e. a yield of 55%.

M.p. 65°–66° C.

$\alpha_D^{25} = +5.8°$ (absolute methanol)

The elementary analysis of this product is

| C$_{27}$H$_{35}$O$_7$N$_3$ (513.6) | C % | H % | N % |
|---|---|---|---|
| calculated : | 63.1 | 6.9 | 8.2 |
| found : | 63.2 | 7.1 | 7.97 |

Hydrochloride of L-Ser (Bzl)-D-iso-Gln-OBzl (II)

1.3 g (2 mmoles) of (I) are treated for 30 minutes with 5 ml of an approximately N solution of hydrochloric acid in acetic acid. The reaction mixture is concentrated to dryness and the product is crystallised in a methanol-ether mixture. 765 mg of product are obtained, i.e. a yield of 85%.

M.p. 158°–161° C.

$\alpha_D^{25} = 8.2°$ (absolute methanol).

Mur-NAc (β-bzl-4,6-bzi)-L-Ser (Bzl)-D-iso-Gln-OBzl (III)

A solution of 471.43 mg (1 mmole) of Mur-NAc (β-bzl-4,6-bzi) in a mixture of acetonitrile and dimethylformamide (2/1, v/v - 10 ml) containing 0.141 ml (1 mmole) of triethylamine is poured into a suspension, maintained at 0° C., of N-ethyl-5-phenylisoxazolium-3'-sulphonate (253 mg - 1 mmole) (reagent D of Woodward, Aldrich) in 10 ml of acetonitrile.

The mixture is stirred at 0° C. until a clear solution is obtained (about 90 minutes), then 450 mg (1 mmole) of (II) in solution in 10 ml of the acetonitrile-dimethylformamide mixture (2/1, v/v) containing 0.141 ml (1 mmole) of triethylamine are added. After stirring overnight at the ambient temperature, the solvents are evaporated under vacuum and the product is precipitated in the dimethylformamide-water mixture. 818 mg of product is obtained, i.e. a yield of 94.3%.

M.p. 181°–186° C.

$\alpha_D^{25} = -17°$ (NN'dimethylformamide).

Mur-NAc-L-Ser-D-iso-Gln (IV)

768 mg of the compound (III) (0.88 mmole) are treated with 30 ml of a 60% solution of acetic acid for an hour at 100° C. After cooling the solution, the acetic acid is evaporated under vacuum and the residue is chromatographed on a column of silica gel (35 g) (chloroform-methanol, 6/2, v/v). The pure fractions are combined, evaporated under vacuum, giving a residue chromatographically pure (plate of silica gel-chloroform-methanol, 6/2, v/v). 287 mg of product are obtained, i.e a yield of 42%.

This product, taken up in 20 ml of glacial acetic acid, is then hydrogenated for 10 hours in the presence of palladium on carbon. After filtration of the catalyst and concentration to dryness of the reaction mixture, the product is obtained by precipitation in an ethanol-acetone-ether mixture. 140 mg of product are obtained, i.e. a yield of 74%. The rotary power is $\alpha_D^{25} = +47.1°$ (glacial acetic acid)

The product is chromatographically homogeneous on plates of silica gel in the mixtures n-butanol-pyridine-acetic acid-water (30/20/6/24, v/v) and n-butanol-acetic acid-water (4/1/5, v/v - upper phase).

The elementary analysis of this product is

| $C_{19}H_{32}O_{12}N_4$ (508.5) | C % | H % | N % |
|---|---|---|---|
| calculated : | 44.88 | 6.34 | 11.02 |
| found : | 44.8 | 6.3 | 11.1 |

Pharmacological properties of the Mur-NAc-L-Ser-D-iso-Gln (1) Determination of the harmlessness of the active principle according to the invention The harmlessness, or on the contrary the toxicity of the Mur-NAc-L-Ser-D-iso-Gln is studied by intravenous injection on mice aged two months. By progressively increasing the doses administered, that for which the mortality of the mice of a single batch is established at 50% ($LD_{50}$) is determined.

For the product studied, it was shown that the $LD_{50}$ is superior to 1 g per kg of animal, which is much greater than the doses for which the product shows its adjuvant properties.

(2) Adjuvant character in aqueous phase

In the series of tests of which the results are indicated hereafter, the influence of the active principle according to the invention on the strength of the anti-albumin antibodies has been studied under the following conditions.

Groups of 8 Swiss mice aged two months receive, by subcutaneous injection, 0.5 mg of antigen constituted by the albumin of bovine serum (BSA) and 0.1 mg of the tested substance in an isotonic saline solution. This high dose of antigen, since it is situated at the limit of the paralysing dose with respect to the immunising response, therefore carries with it a weak response or no response to the antigen alone in the tests; it then constitutes a severe criterion for showing the activity of an adjuvant substance. Thirty days later, the mice receive a further dose containing 0.1 mg of the same antigen.

The strength of the antibody is determined by passive hemagglutination by using the red blood corpuscles of sheep treated with formalin and recovered from the antigen studied by the method described by A. A. Hirata and M. W. Brandiss (J. Immunol., 100, 641–648, 1968). The taking of the blood occurred 14, 28, 34 and 36 days after the first injection.

By way of comparison, the mice receive, instead of the Mur-NAc-L-Ser-D-iso-Gln, either lipopolysaccharides (LPS) (extract of S. Enteritidis by the water-phenol method), or the adjuvant denoted by the name "WSA" and described by Adam et al. [Infect. Immun. (1973) 7, 855–861]. The control mice only received the antigen.

The results of these tests are given in the following Table.

Table 1

|  | Strength of antibody | 14th day | 28th day | 34th day | 36th day |
|---|---|---|---|---|---|
| Control BSA |  | <3 | <3 | <3 | <3 |
| BSA + LPS | (100μg) | <3 | 6 | 50 | 1310 |
| BSA + WSA | (300μg) | <3 | <3 | <3 | 6 |
| BSA + Mur-NAc-L-Ser-D-iso-Gln | (100 μg) | 12 | 25 | 1600 | 1600 |

These tests were carried out again with limitation of the dose of antigen in the first injection to 0.05 mg, the other conditions being the same. This weaker dose of antigen gives by itself a positive response with the controls which have received the antigen without adjuvant. It thus allows to be shown a substance which inhibits the response of immunising the disorder. Moreover, an adjuvant substance, under these conditions, always increases the strength of antibody with respect to that of the controls.

In these tests, the determination of the strength of antibody has been effected simultaneously by passive hemagglutination (PA) and by the method of fixation of the antigen by the serum (ABC), such as described by P. Minden and S. Parr (Handbook of Exp. Immunol., P. 463, D. M. Weir ed. Blackwell Scient. Pub. Oxford and Edinburgh, 1967).

The results of these tests are shown in the following Table.

Table 2

|  | Strength of antibody | 14th day | | 28th day | | 34th day | | 36 day | | 42nd day |
|---|---|---|---|---|---|---|---|---|---|---|
|  |  | PA | ABC | PA | ABC | PA | ABC | PA | ABC | PA |
| BSA (control) |  | <3 | <20 | <3 | <20 | 6 | <20 | 50 | 25 | 25 |
| BSA + LPS |  | <31 | <20 | 25 | <20 | 400 | 300 | 3200 | 500 | 800 |
| BSA + WSA | (100 μg) | <31 | <20 | <3 | <20 | 6 | <20 | 3 | <20 | 3 |
| BSA + WSA | (300 μg) | <3 | <20 | <3 | <20 | <3 | <20 | <3 | <20 | <3 |
| BSA + Mur-NAc-L-Ser-D-iso-Gln | (100 μg) | <3 | <20 | 3 | <20 | 50 | <20 | 800 | 230 | 260 |

These results show that the Mur-NAc-L-Ser-D-iso-Gln, administered in saline isotonic solution, causes a considerable increase in the strength of antibody formed, although, under the same conditions, the WSA is practically inactive.

In the second series of tests, for which the dose of antigen, in the first injection, is weak, the presence of WSA even seems to inhibit the formation of antibody, although the Mur-NAc-L-Ser-D-iso-Gln, on the contrary, favours the appearance of the antibodies.

The Mur-NAc-L-Ser-D-iso-Gln may be considered in a general way as comparable to the LPS for its capacity to stimulate the formation of the antibodies, but, contrary to the LPS, it is without toxicity.

We claim:

1. Esters of 2-(2-acetamido-2-deoxy-3-O-D-glucopyranosyl)-D-propionyl-L-alanyl-D-glutamic acid and of 2-(2-acetamido-2-deoxy-3-O-D-glucopyranosyl)-D-propionyl-L-alanyl-D-isoglutamine corresponding to the formula

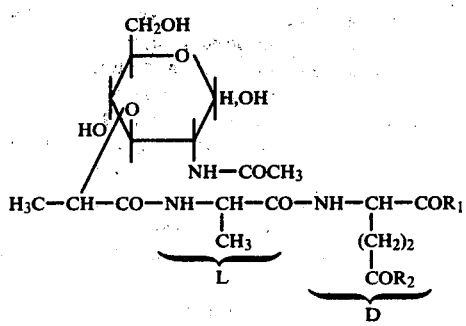

in which $R_1$ is $-OC_nH_{2n+1}$, with n=1, 2 or 3, or $-NH_2$, $R_2$ is $-OC_pH_{2p+1}$, with p=0, 1, 2 or 3, p being not equal to 0 when $R_1$ is $-NH_2$.

2. The α-methyl ester of 2-(2-acetamido-2-deoxy-3-O-D-glucopyranosyl)-D-propionyl-L-alanyl-D-glutamic acid, corresponding to the abridged formula Mur-NAc-L-Ala-D-Glu-α-OCH₃.

3. The methyl diester of 2-(2-acetamido-2-deoxy-3-O-D-glucopyranosyl)-D-propionyl-L-alanyl-D-glutamic acid corresponding to the abridged formula Mur-NAc-L-Ala-D-Glu-(OCH₃)₂.

4. The methyl ester of the 2-(2-acetamido-2-deoxy-3-O-D-glucopyranosyl)-D-propionyl-L-alanyl-D-isoglutamine corresponding to the abridged formula Mur-NAc-L-Ala-D-iso-Gln-(OCH₃).

5. 2-(2-acetamido-2-deoxy-3-O-D-glucopyranosyl)-D-propionyl-L-alanyl-D-(α-methylamide)-glutamic acid, which corresponds to the formula

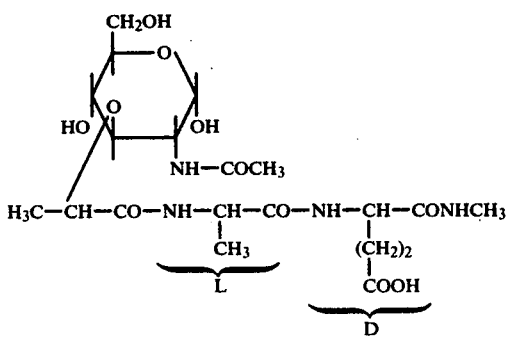

6. 2-(2-acetamido-2-deoxy-3-O-D-glucopyranosyl)-D-propionyl-L-seryl-D-isoglutamine, which corresponds to the formula

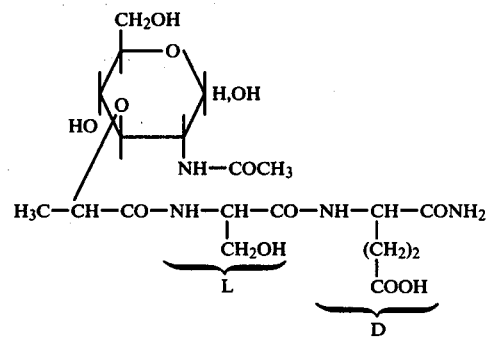

and 2-(2-acetamido-2-deoxy-3-O-D-glucopyranosyl)-D-propionyl-L-seryl-D-glutamic acid corresponding to the formula

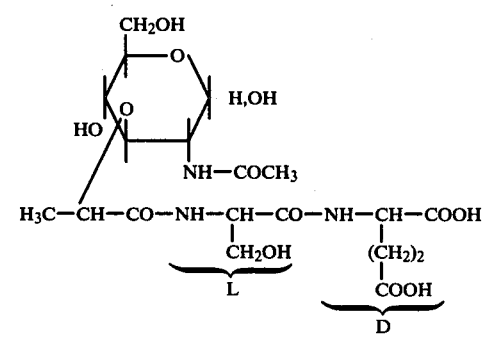

their mono and di methyl, ethyl, propyl ester derivatives and their amide derivatives possibly N substituted by methyl rests.

7. The compound, 2-(2-acetamido-2-deoxy-3-O-D-glycopyranosyl)-D-propionyl-L-seryl-D-isoglutamine.

8. The therapeutic composition which comprises a therapeutically acceptable carrier and in a therapeutic amount, the compound of claim 7.

9. A pharmaceutical composition which comprises an innert carrier and, in an effective amount, an ester of claim 1.

10. The pharmaceutical composition which comprises an innert carrier and, in an effective amount, an ester of claim 2.

11. The pharmaceutical composition which comprises an innert carrier and, in an effective amount, an ester of claim 3.

12. The pharmaceutical composition which comprises an innert carrier and, in an effective amount, an ester of claim 4.

13. An anti-infectious medicinal composition which comprises a pharmaceutically acceptable carrier and an ester of claim 1.

14. An anti-infectious medicinal composition which comprises a pharmaceutically acceptable carrier and an ester of claim 2.

15. An anti-infectious medicinal composition which comprises a pharmaceutically acceptable carrier and an ester of claim 3.

16. An anti-infectious medicinal composition which comprises a pharmaceutically acceptable carrier and an ester of claim 4.

17. The composition of claim 13 wherein the ester is in an amount of about 50 to about 2000 ug.

18. The composition of claim 9 wherein the carrier is oil-containing.

19. The composition of claim 9 wherein the carrier is an aqueous carrier free of oil.

20. The composition of claim 10 wherein the carrier is an aqueous carrier free of oil.

21. The composition of claim 11 wherein the carrier is an aqueous carrier free of oil.

22. The composition of claim 12 wherein the carrier is an aqueous carrier free of oil.

23. The composition of claim 19 wherein the carrier is an isotonic saline or glucose solution.

24. The method of controlling a pathogenic infection which comprises administering to a warm blooded animal in an amount effective to control bacteria, an ester of claim 1.

25. The method of controlling a pathogenic infection which comprises administering to a warm blooded animal in an amount effective to control bacteria, an ester of claim 2.

26. The method of controlling a pathogenic infection which comprises administering to a warm blooded animal in an amount effective to control bacteria, an ester of claim 3.

27. The method of controlling a pathogenic infection which comprises administering to a warm blooded animal in an amount effective to control bacteria, an ester of claim 4.

28. The method of claim 24 wherein the administration is oral.

29. The method of claim 25 wherein the administration is oral.

30. The method of claim 26 wherein the administration is oral.

31. The method of claim 27 wherein the administration is oral.

32. The pharmaceutical composition of claim 9 which comprises an immunising agent.

33. The pharmaceutical composition of claim 10 which comprises an immunising agent.

34. The pharmaceutical composition of claim 11 which comprises an immunising agent.

35. The pharmaceutical composition of claim 12 which comprises an immunising agent.

36. The therapeutical composition which comprises a therapeutically acceptable carrier and in a therapeutically acceptable amount, the compound of claim 5.

37. The therapeutical composition of claim 36 wherein the carrier is aqueous and free of oil.

38. The therapeutical composition of claim 36 wherein the carrier contains oil.

39. The therapeutical composition which comprises a therapeutically acceptable carrier and in a therapeutically acceptable amount, the compound of claim 6.

40. The therapeutical composition of claim 39 wherein the carrier is aqueous and free of oil.

41. The therapeutical composition of claim 38 wherein the carrier contains oil.

* * * * *